(12) United States Patent
Welander et al.

(10) Patent No.: US 10,626,034 B2
(45) Date of Patent: Apr. 21, 2020

(54) FREE-FLOWING CARRIER ELEMENTS

(71) Applicant: Veolia Water Solutions & Technologies Support, Saint-Maurice (FR)

(72) Inventors: Thomas Welander, Furulund (SE); Maria Piculell, Malmö (SE)

(73) Assignee: Veolia Water Solutions & Technologies Support, Saint-Maurice (FR)

( * ) Notice: Subject to any disclaimer, the term of this patent is extended or adjusted under 35 U.S.C. 154(b) by 29 days.

(21) Appl. No.: 15/039,522

(22) PCT Filed: Nov. 28, 2014

(86) PCT No.: PCT/EP2014/075958
§ 371 (c)(1),
(2) Date: May 26, 2016

(87) PCT Pub. No.: WO2015/082349
PCT Pub. Date: Jun. 11, 2015

(65) Prior Publication Data
US 2016/0376175 A1  Dec. 29, 2016

(30) Foreign Application Priority Data
Dec. 2, 2013  (SE) ...................... 1351432

(51) Int. Cl.
*C02F 3/10* (2006.01)
*C02F 3/08* (2006.01)
(Continued)

(52) U.S. Cl.
CPC ............. *C02F 3/109* (2013.01); *B01J 19/305* (2013.01); *C02F 3/08* (2013.01); *C02F 3/108* (2013.01);
(Continued)

(58) Field of Classification Search
CPC ... C02F 3/109; C02F 3/08; C02F 3/108; B01J 19/305; C12N 11/04; C12N 11/08
(Continued)

(56) References Cited

U.S. PATENT DOCUMENTS 4,537,731 A * 8/1985 Billet ..................... B01J 19/30
261/94
5,618,430 A    4/1997 Fuchs
(Continued)

FOREIGN PATENT DOCUMENTS

CN    201896101 U    7/2011
DE    3017439 A1    11/1981
(Continued)

OTHER PUBLICATIONS

PCT International Preliminary Report on Patentability for Application No. PCT/EP2014/075958, dated Dec. 1, 2015, including Applicant Response to Written Opinion of the European Patent Office acting as the International Searching Authority filed Oct. 1, 2015.
(Continued)

*Primary Examiner* — Claire A Norris
(74) *Attorney, Agent, or Firm* — Honigman LLP; Anna M. Budde

(57) ABSTRACT

A carrier element (1; 10; 20) for growth of biofilm thereon is designed for free-flowing in liquid to be purified and has surfaces (3; 13) for biofilm growth which are protected from the abrasion from other carrier elements or surfaces in a container containing the liquid to be purified by ridges (4; 12) having a height corresponding to a desired thickness of a biofilm intended to grow on the protected surfaces (3; 13). The ratio between the surfaces (3; 13) for biofilm growth and the area of the ridges ranges from 1:1 to 1:20.

7 Claims, 4 Drawing Sheets

(51) Int. Cl.
  *C12N 11/08* (2020.01)
  *B01J 19/30* (2006.01)
  *C12N 11/04* (2006.01)

(52) U.S. Cl.
  CPC .............. *C12N 11/04* (2013.01); *C12N 11/08* (2013.01); *C02F 3/085* (2013.01); *Y02W 10/15* (2015.05)

(58) Field of Classification Search
  USPC ........................................................ 210/150
  See application file for complete search history.

(56) References Cited

U.S. PATENT DOCUMENTS

| | | | |
|---|---|---|---|
| 5,985,148 | A | 11/1999 | Liu |
| 7,189,323 | B2 * | 3/2007 | Lofqvist .................. C02F 3/10 210/150 |
| 8,241,717 | B1 | 8/2012 | Anderson |
| 2003/0127378 | A1 | 7/2003 | Shechter et al. |
| 2005/0072732 | A1 | 4/2005 | Lofqvist et al. |
| 2008/0038554 | A1 | 2/2008 | Cantwell |
| 2009/0115077 | A1 | 5/2009 | Niknafs et al. |
| 2010/0101994 | A1 | 4/2010 | Poltorak |
| 2012/0055870 | A1 | 3/2012 | Pajuniemi et al. |

FOREIGN PATENT DOCUMENTS

| | | |
|---|---|---|
| DE | 202006011984 U1 | 11/2006 |
| DE | 102009043110 A1 | 3/2011 |
| EP | 0058974 A1 | 9/1982 |
| EP | 0142123 A1 | 3/1988 |
| EP | 1340720 A1 | 9/2003 |
| EP | 1431252 A1 | 6/2004 |
| EP | 2119499 A1 | 11/2009 |
| EP | 2251308 A1 | 11/2010 |
| FR | 0850478 A1 | 7/2009 |
| GB | 1439745 A | 6/1976 |
| JP | H01-249189 A | 10/1989 |
| JP | 2003-211155 A | 7/2003 |
| NL | 7306968 A | 11/1973 |
| WO | 9111396 A1 | 8/1991 |
| WO | 9610542 A1 | 4/1996 |
| WO | 0015565 A1 | 3/2000 |
| WO | 2004071973 A1 | 8/2004 |
| WO | 2007077298 A1 | 7/2007 |
| WO | 2013149662 A1 | 10/2013 |

OTHER PUBLICATIONS

D. Dengler et al., "Einsatz von Schwebekörper zur Erhöhung der," Bundesministerium für Forschung und Technologie, Forschungsbericht 02 WA 8538, Jan. 1988, pp. 12 and 13.

"Notice of Reasons for Rejection," Japanese Patent Application No. 2016-536234 (dated Nov. 20, 2018).

* cited by examiner

FREE-FLOWING CARRIER ELEMENTS

CROSS-REFERENCE TO RELATED APPLICATIONS

This application is a 35 USC § 371 United States National Phase Application of PCT International Application No. PCT/EP2014/075958 filed Nov. 28, 2014, which claims priority to Swedish Application No. SE 1351432-8 filed Dec. 2, 2013.

FIELD OF THE INVENTION

The present invention relates to a carrier element for growth of biofilm thereon, said carrier elements being designed for free-flowing in liquid to be purified and having surfaces for biofilm growth which are protected from the abrasion from other carrier elements or surfaces in a container containing the liquid to be purified.

BACKGROUND OF THE INVENTION

It is known that in biological treatment of water or wastewater, the water is passed through some type of reactor or several reactors (a vessel or another space) wherein micro-organisms are utilized for converting pollutants in the water to harmless end products such as carbon dioxide and water. The treatment can be performed under supply of air (aerobically) or without supply of air (anaerobically) or without supply of air but with presence of significant amounts of nitrate (anoxically). In order to increase the efficiency of the treatment process, it is common to aim at a high content of active micro-organisms in the process by preventing such organisms to escape together with the treated water, either by allowing the micro-organisms to grow suspended in the reactor and separating them from the water in a separation stage after the reactor and returning the micro-organisms to the reactor (e.g. the activated sludge process), or by introducing some kind of support material into the process on the surfaces of which the micro-organisms can grow as a biofilm and thus be retained in the process (the biofilm process). There are also mixtures of these two process types, referred to as hybrid processes, wherein the support material is introduced into the activated sludge process so that suspended micro-organisms as well as biofilm growing microorganisms can be utilized in the process.

The biofilm process has several advantages compared to the activated sludge process. For example, higher loads can be applied and the biofilm processes are substantially less sensitive to variations and disturbances. Most conventional biofilm processes are based on packing of carrier material in the treatment reactor, said material comprising fill bodies or blocks which are maintained fixed and immovable in the process. These embodiments of the process involve the risk of clogging of the biofilm bed by biomass or another particulate material and formation of dead zones in the process, wherein the contact between the water and the active micro-organisms is unsatisfactory.

In another type of biofilm process, which has become very successful during the last 20 years, a carrier material which is kept in suspension and in movement is utilized in process referred to as the MBBR process, i.e. "Moving Bed Biofilm Reactor". The carrier material with micro-organisms growing thereon is maintained in the process by passing outgoing water through a strainer (sieve or grid) having an aperture diameter or slot width which is so small that the carrier material cannot pass therethrough. The advantage of this kind of process is i.a. that the risk of clogging of the bed and formation of dead zones is eliminated.

The use of a carrier material which is kept in suspension and movement in the process was originally reported for different hybrid process applications, i.e. suspended carriers were supplied to activated sludge processes in order to improve the function thereof. Carriers which have been used for this purpose include pieces of foamed rubber (EP 0 142 123), different types of cylindrical fill bodies (Bundesministerium für Forschung and Technologie, "Einsatz von Schwebekörper zur Erhöung der." by Dr. D. Dengler, H. Lang, A. Baum, Forschungsbericht 02 WA 8538, January 1988, pages 12 and 13), carriers including hemispherical bodies having inner walls (DE 30 17 439), "hedgehog-like" carriers, perforated spheres, and crossed plates (EP 0 058 974).

WO 96/10542 discloses another embodiment that is related to the foamed rubber pieces of EP 0 142 123. Thin flakes of foamed plastic are used that provide protected surface area in the randomly formed pores of the carriers.

Since the carriers in the MBBR process are exposed to repeated collisions with each other and other surfaces in the reactor, the surfaces that are exposed to other carriers or other surfaces in the reactor are kept clean from biofilm growth. The efficiency of the process therefore is highly dependent on the area that is protected against collisions, for example in inner passages or compartments in the carriers.

Another embodiment of MBBR carriers is disclosed in FR 0850478, which concerns a method for biological treatment of water in which is used carriers, which are plate-formed bodies with protrusions jutting out from the plates, said protrusions being separate from each other and where the protrusions and the body itself both provide protected surface area. This embodiment is claimed to give mass transfer advantages when the carriers are stacking close together as the water can still move between the body and protrusions.

EP 1 431 252 discloses a carrier element that is probably suitable for an MBBR process. The carrier element is said to have excellent properties when it comes to the ability to retain air bubbles, meaning that the aeration process will be more efficient.

WO 00/15565 discloses a "radial flow bioreactor", usable e.g. for treatment of wastewater. In FIGS. 13-15 thereof, different embodiments of carrier elements exhibiting growth areas allowing for a biofilm having a desired thickness are shown. It is, however, highly unlikely that these carrier elements can be used as free-flowing carrier elements. In any event, they are extremely inefficient, since the protected area amounts to less than 50% of the area of the carrier element's surface area.

One problem with all known carriers for water treatment is that they allow for practically unlimited growth of the thickness of the bioactive microbe layer. This might lead to problems with restricted flow and/or anaerobic zones in the biofilm, even in an environment designed to be aerobic.

SUMMARY OF THE INVENTION

The above and other problems are solved, or at least mitigated, by providing a carrier element wherein the ratio between the surfaces for biofilm growth and the area of the ridges protecting the surfaces for microfilm growth ranges from 1:1 to 20:1.

In order to get a controlled biofilm thickness, the height of the ridges may correspond to the desired thickness of a biofilm intended to grow on the protected surfaces.

Tests have shown that the ridges height may be within the interval of 0.05-1.0 mm, preferably 0.1-0.5 mm, most preferably 0.15-0.45 mm.

In one embodiment of the invention, said carrier element may be in the form of a plate with a grid on each side, said grid forming well defined indentations to protect biofilm growth, and where the depth of said indentations decides the thickness of said protected biofilm.

In order to avoid sharp edges, said plate may be of round or oval shape.

In order to improve aeration, said plate may be saddle shaped.

In one embodiment of the invention, said pattern may be in the shape of a grid with square or rectangular indentations.

In another embodiment of the invention, said pattern may be in the shape of a honeycomb with hexagonal indentations.

In still another embodiment of the invention, the carrier element may be in the shape of a profile with longitudinal inner channels, wherein, the longitudinal inner channels contains a multitude of longitudinal retention walls extending from the inner channel walls towards the center of the longitudinal inner channels, longitudinal grooves are formed between longitudinal retention walls, rod-like cleaning elements can enter the center of the longitudinal inner channels, said rod-like cleaning elements cannot enter said longitudinal grooves, the longitudinal grooves protects biofilm growth along the longitudinal inner channel walls, the protected biofilm thickness along the longitudinal inner channel walls is determined by the height of the longitudinal retention walls.

The rod-like cleaning elements may be arranged along the periphery of the carrier element, on part of or all the carrier elements.

The rod-like cleaning elements may also be provided on another structure of in the reactor than the carrier element, for example in the shape of brushlike structures inside the reactor.

The carrier element may be in any shape, for example hexagonal, squared or round.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Figure 1:
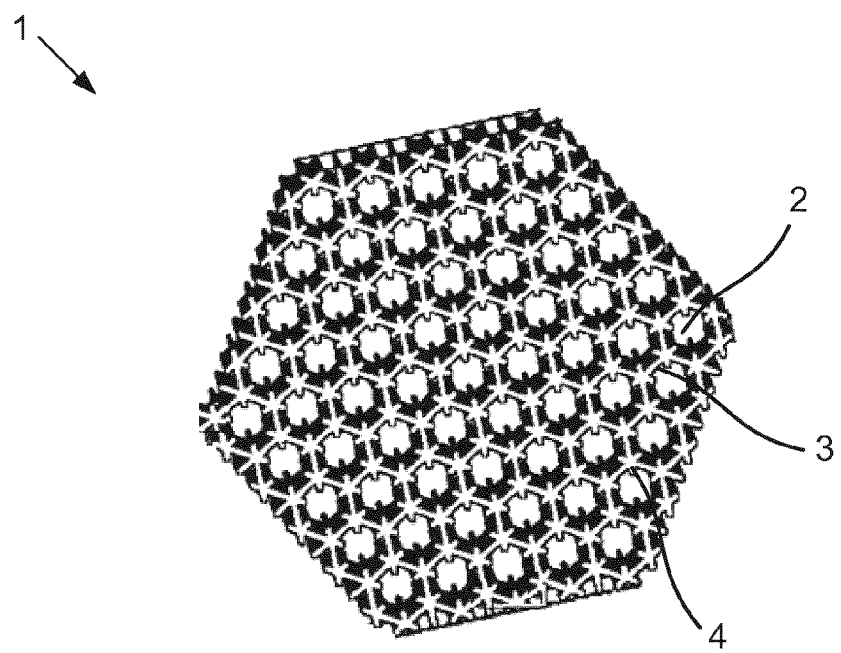
FIG. 1 is a schematic perspective view showing a hexagonal carrier element according to a first embodiment of the invention.

A first embodiment the present invention is shown in FIG. 1 and relates to a carrier element 1 for allowing growth thereon of a biologically active layer of microbes. The carrier element 1 comprises a multitude of through holes 2, each through hole 2 being limited by walls 3 and ridges 4 extending along a length of the through hole 2. The through holes 2 and their ridges 4 are arranged to be cleaned by a rod-like structure (not shown) having a diameter fitting within the area defined by the ridges 4. In the shown embodiment, the through holes 2 are hexagonally shaped and arranged, but other arrangements are also possible within the scope of the invention.

The arrangement with a rod-like cleaning element and the ridges of the holes has the effect that a microbial film growing in the holes will be limited with regards to its thickness.

Figure 2:
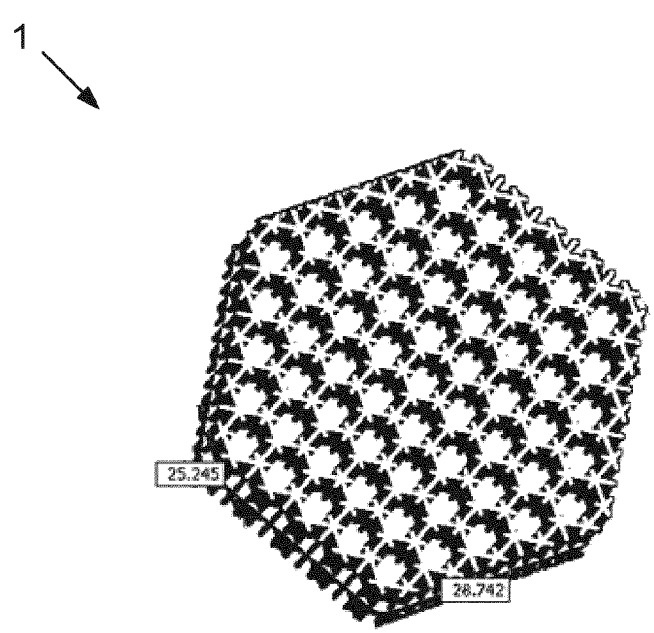
FIG. 2 is a schematic perspective view showing a hexagonal carrier element according to a second embodiment of the invention.

FIG. 2 shows an embodiment that is similar to the embodiment of FIG. 1, however with a dividing wall extending between two identical elements provided with holes having a shape corresponding to the through holes of FIG. 1.

Figure 3:
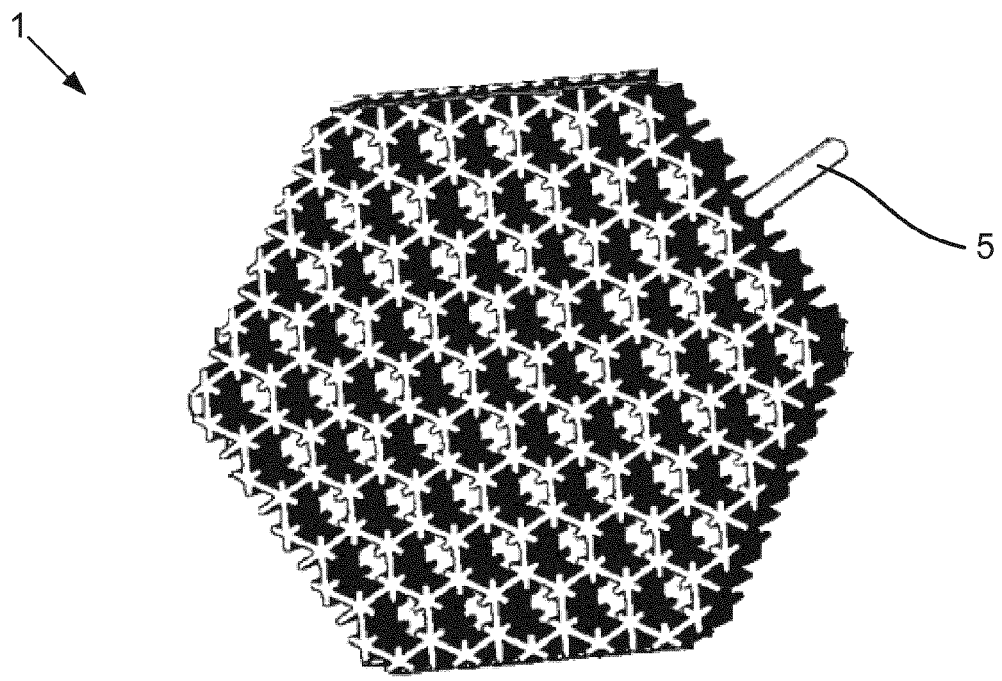
FIG. 3 is a schematic perspective view showing a hexagonal carrier element according to a third embodiment of the invention.

FIG. 3 shows an embodiment that is similar to the embodiment of FIGS. 1 and 2, however with a rod-like cleaning element 5 extending from an outer surface of the carrier 1.

Figure 4:
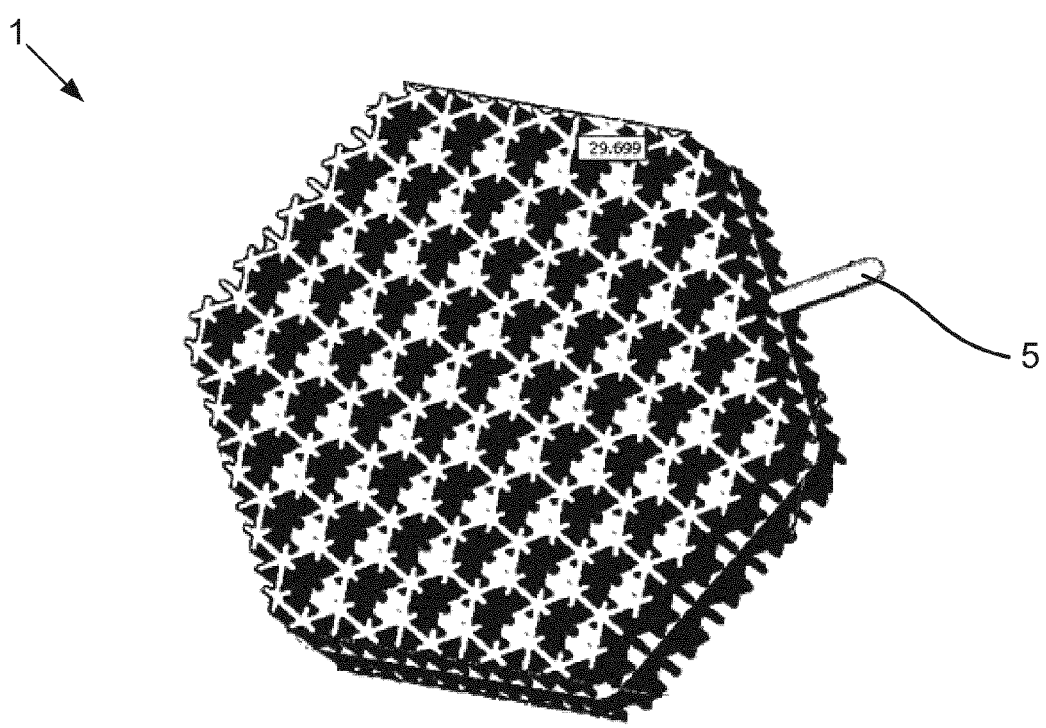
FIG. 4 is a schematic perspective view showing a hexagonal carrier element according to a fourth embodiment of the invention.

FIG. 4 shows an embodiment that is similar to the embodiment of FIG. 2, however with a rod-like cleaning element 5 extending from an outer surface of the carrier 1.

Figure 5:
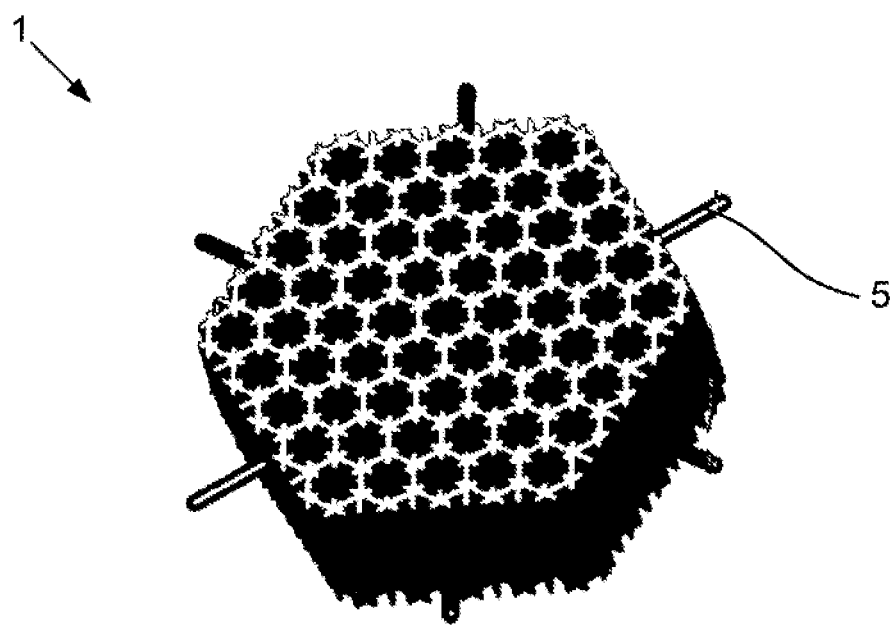
FIG. 5 is a schematic perspective view showing a hexagonal carrier element according to a fifth embodiment of the invention.

FIG. 5 shows still another embodiment having six rod-like cleaning elements 5.

During operation the elements will float around, contacting other elements and surfaces in a reactor (not shown). The inner surfaces of the through holes will be protected from wear, however the rod-like cleaning elements 5 described in embodiments 3 to 5, having a diameter fitting within the area defined by the ridges 4, will be able to scrape out the biofilm in the center of the through holes, leaving a protected biofilm layer with a thickness defined by the height of the ridges 4 extending along a length of the through hole 2.

The elements 1 can be manufactured from e.g. polyethylene plastic or polypropylene plastic by extrusion or injection molding, they may have a thickness of 2 to 20 mm, a diameter of 10 to 50 mm, a through hole diameter of 2 to 5 mm, wherein the ridges may extend 0.1 to 0.5 mm from an internal surface of the through hole. The rod like cleaning element 5 has preferably a diameter such that it may enter the holes, i.e. its diameter is smaller than the hole diameter subtracted by the height of the ridges 4. Its length is preferably somewhat larger than half of the thickness of the carrier.

The elements 1 described in embodiments 2, 3 and 6 can have a small protrusion (not shown) on the dividing wall in the bottom of the holes. This small protrusion may extend 0.1 to 0.5 mm from the dividing wall of the hole and have a diameter smaller than the hole diameter subtracted by the height of the ridges 4. The dividing wall surface of the hole will be protected from wear from the rod-like cleaning element 5, leaving a protected biofilm layer with a thickness defined by the height of the small protrusion.

As a result of this the biofilm growing within the holes will have a limited thickness, thereby avoiding anaerobic portions of the biofilm.

Figure 6:
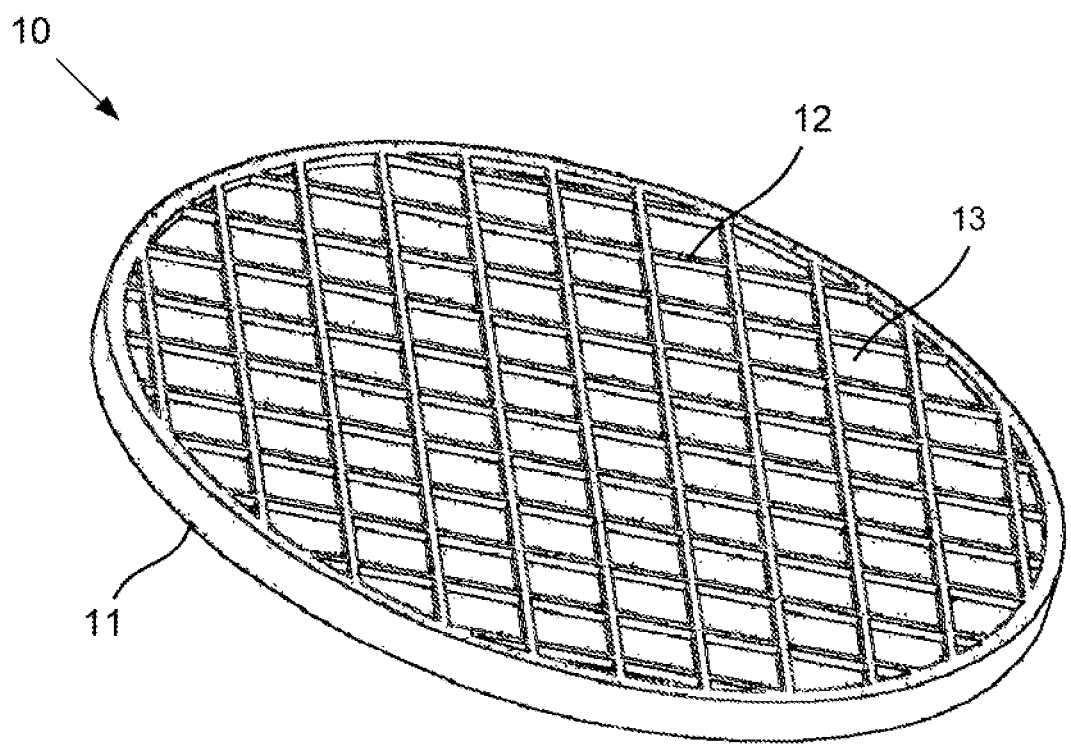
FIG. 6. is a schematic perspective view showing a flat round carrier element according to a sixth embodiment of the invention.

In FIG. 6, a carrier 10 according to another embodiment of the present invention is shown. The carrier 10 comprises a disc-like body 11 comprising a grid 12 of ridges 4 extending over the entire area of the disc-like body 11. The ridges 4 of the grid 12 have a height over the disc-like body 11 corresponding to a desired thickness of a biofilm growing thereon. It should be noted that the disc-like body should have a shape avoiding sharp corners, i.e. a circular or oval shape, since sharp corners will scrape off biofilm from the disc-like body, even if protected by the grid 12 of ridges 4.

During operation, wherein a large number of carriers according to this embodiment are free-floating in the reactor, biofilm growing on the surface thereof will be scraped off. However, due to the provision of the grid 12 and the fact that there are no sharp corners, areas 13 between the ridges 4 of the grid 12 will be protected from wear. However, if the biofilm thickness becomes too large the excess will be scraped off. Accordingly, the biofilm thickness may be controlled in an efficient manner.

Figure 7:
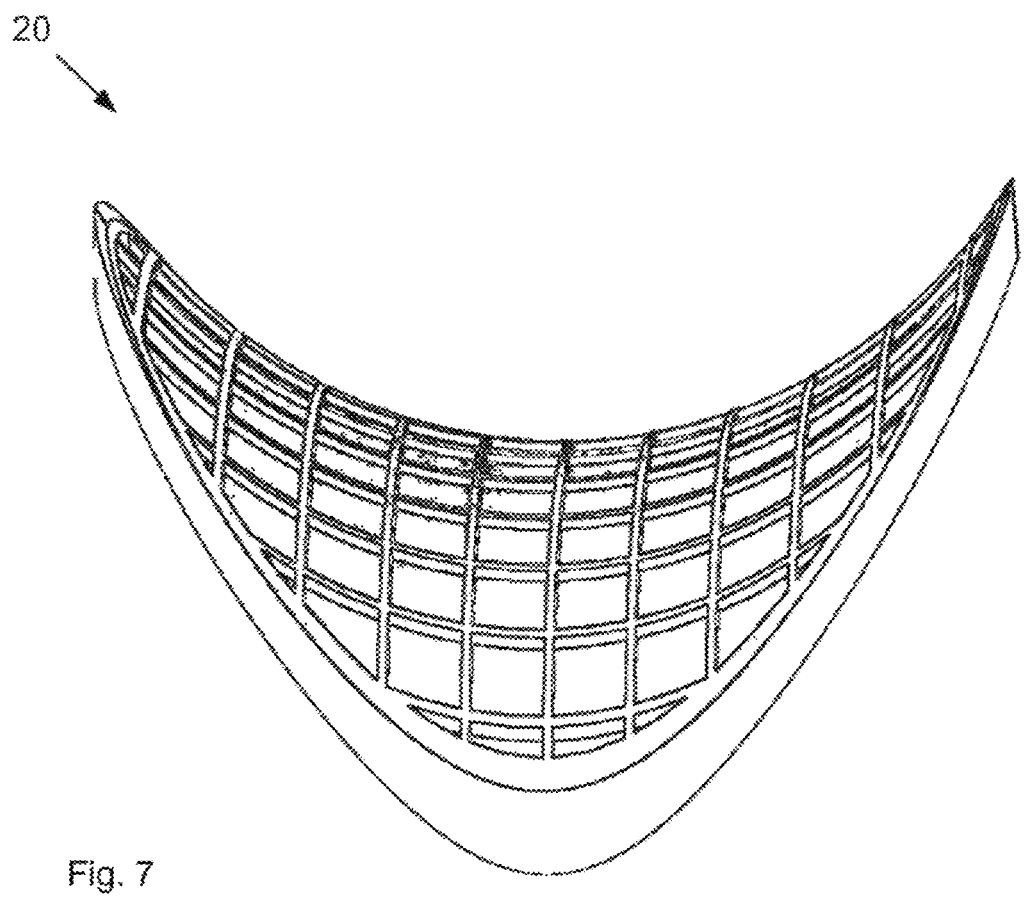
FIG. 7. is a schematic perspective view showing a saddle shaped carrier element according to a seventh embodiment of the invention.

In FIG. 7, a carrier 20 is shown, the carrier 20 being substantially identical to the carrier 10 of FIG. 6, however, formed into a saddle-like configuration. This configuration has been shown to perform excellently in terms of aeration properties.

Figure 8:
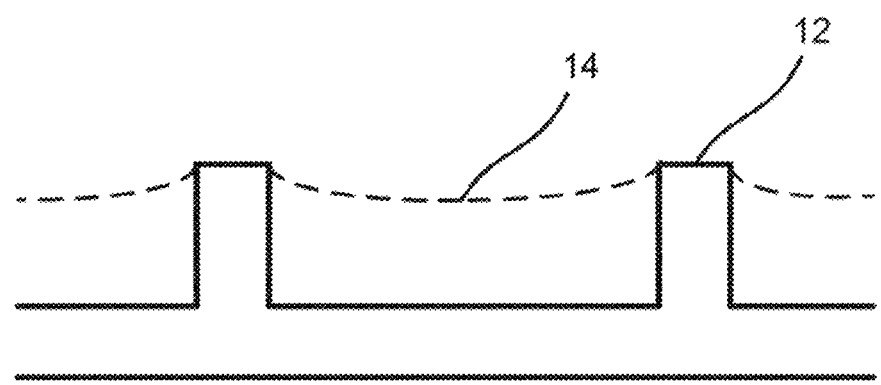
FIG. 8. is a schematic cross section view showing a carrier element with an arched biofilm surface layer.

FIG. 8 illustrates when a biofilm surface between the ridges 4 of the grid 12 on a disc-like body 11 carrier has not been scraped off at a straight angle. When two carrier elements 10 have scraped against each other, the circular or oval shape of the disc-like bodies 11 may leave a correspondingly arched biofilm surface 14 shape between the ridges 4 of the grid 12. The shape of such an arched surface 14 will depend on the diameter of the disc-like body and the grid 12 density.

The carriers 10 and 20 may be manufactured by injection molding. They may have a diameter of 10 to 50 mm, a grid 12 density of 5 to 10 mm and a ridge 4 height of 0.05 to 1.0 mm. The thickness of the body is preferably as thin as possible with regards to the strength thereof. Another manufacturing method may be to roll a plate of plastic such that ridges 4 thereon are formed and thereafter stamp carriers of the desired shape and size from the rolled plate.

The surface area for biofilm growth is primarily the wall 3 or area 13 of the carrier elements. The ridge 4 and grid 12 constitute similar or smaller biofilm growth area and primarily protects and define the thickness of the biofilm.

The ratio of biofilm growth area between the protected surfaces walls 3 and areas 13 between the ridges 4 in comparison to the ridges 4 and the grid 12 of ridges 4 of the carrier elements 1 and 10 and 20 is in the range of 1:1 to 20:1.

Because they are the engine that drives biological wastewater treatment, it is critical to closely monitor the quantity and quality of microorganisms in bioreactors.

Earlier developments of the MBBR-process and carrier elements has been solely focused on the protective surface provided by the carrier material and to some extent to how the carrier elements should be formed to increase the mass transport to the biofilm, when the biofilm has an extensive thickness.

A major limitation of all prior art carriers and MBBR processes is that the thickness of the biofilm is not controlled to a range where the mass transfer is effective throughout the biofilm, thus only the outer part of the biofilm is utilizing for the desired reactions.

When the biofilm grows thick on the carrier elements, the effective area of the biofilm exposed to the environment is reduced, making a large portion of biomass inactive with respect to the desired reactions and the MBBR process efficiency decreases. The process can thus exhibit a varying effectiveness depending on how the biofilm develops and a complete in-growth of biofilm in the support elements results in a drastic reduction in efficiency. For a thick biofilm, reactions averse to the MBBR-process may take place further into the biofilm, for example the reduction of sulfate to hydrogen sulfide. These problems are well known, but no solution has existed for controlling them.

When the over-growth of the inert carrier elements becomes acute, different types of washing devices has been used to mechanically knock away the biofilm from the carriers. For the individual carrier elements, however, the result of the cleaning is random, and the biofilm is not controlled to an optimum thickness. The present invention relates to a carrier element in which thickness of the biofilm in a MBBR process can be predetermined and maintained in an optimum range for the desired reactions.

The wear which occurs when the carrier elements moves against other carrier elements or other surfaces in the process has previously been considered as a disadvantage of the MBBR process, since it limits the size of the area of the support material which can be colonized with biofilm compared with other biofilm processes where the carriers are stationary and all surfaces are colonized. The general solution according to the invention is to instead use this wear to provide a biofilm with controlled thickness within an optimum range for the reactions to be achieved, which provides significant advantages over prior MBBR processes as well as other biofilm processes.

In comparisons between the invention and the prior embodiments, it has been found that it is equally important to keep the "protected biofilm thickness" of a carrier element within the optimal range as achieving a maximum protected surface of the material.

It has been shown that the efficiency of the process is in practice determined by the amount of biomass that actively participates in the desired reactions and this is found in the part of the biofilm which is reached by the reactants which are to be renewed. Because of the nature of the biofilm process, a carrier material surface which stops the liquid flow, the transport of reactants into the biofilm will be limited by the diffusion rates for the substances in question. This type of mass transport limitation in a biofilm applies to all kinds of substrates, such as oxygen in aerobic processes, volatile fatty acids in anaerobic processes, the nitrification of ammonium and phosphate in the biological phosphorus removal.

More particularly, MBBR trials according to the present invention has shown that in order to achieve a maximum active biofilm, the thickness thereof has to be kept in the range of 0.05-1.0 mm, preferably in the range of 0.1-0.5 mm, in particular in the range of 0.15 to 0.45 mm.

For biofilm thinner than 0.05 mm, the amount of active biomass is limited by the biofilm thickness, so that full capacity is not reached. For biofilm thicker than 1.0 mm, there is a significant amount of inactive biomass in the interior of the biofilm and unwanted reactions begin to assert themselves.

The protected biofilm thickness is the thickness to which biofilm can grow on the support element without being subjected to scraping against other surfaces in the process, the surfaces of other carriers, reactor walls or other parts of the reactor. The protected biofilm thickness will thus depend on both the carrier material design as well as the design of other parts of the reactor.

The present invention has the advantage over the prior art that it provides a carrier element which uses the wear and tear from when the carrier elements moves against other carrier elements or other surfaces in the process to control the thickness of the biofilm within an optimum range for the reactions to be achieved, which provides significant advantages over prior MBBR processes as well as other biofilm processes.

Although the present invention has been described above with reference to specific embodiments, it is not intended to be limited to the specific forms set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. Carrier element for growth of biofilm thereon, comprising protected surfaces for biofilm growth between ridges which are protected by the ridges from abrasion from other carrier elements or surfaces while free flowing in a container containing a liquid to be purified,
   wherein said carrier element is in a form of a plate with a pattern on each side, said pattern being a grid of the ridges,
   wherein the ratio between area of the protected surfaces for biofilm growth between the ridges and side area of the ridges ranges from 1:1 to 20:1, and
   a height of the ridges, which corresponds to a desired thickness of a biofilm intended to grow on the protected surfaces, is within the interval of 0.05 to 1.0 mm.

2. Carrier element according to claim 1, wherein the height of the ridges, which corresponds to the desired thickness of a biofilm intended to grow on the protected surfaces, is within the interval of 0.1 to 0.5 mm.

3. Carrier element according to claim 1, wherein the height of the ridges, which corresponds to the desired thickness of a biofilm intended to grow on the protected surfaces, is within the interval of 0.15 to 0.45 mm.

4. Carrier element according to claim 1, wherein said plate is of round or oval shape.

5. Carrier element according to claim 1, wherein said plate is saddle shaped.

6. Carrier element according to claim 1, wherein the protected surfaces for biofilm growth between the ridges are square or rectangular.

7. Carrier element according to claim 1, wherein said grid is in a shape of a honeycomb with hexagonal protected surfaces for biofilm growth between the ridges.

* * * * *